(12) United States Patent
Fink

(10) Patent No.: US 10,458,848 B2
(45) Date of Patent: Oct. 29, 2019

(54) DENTAL IMAGING AND ILLUMINATION DEVICE

(71) Applicant: 3M INNOVATIVE PROPERTIES COMPANY, St. Paul, MN (US)

(72) Inventor: Johannes Fink, Bergheim (DE)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 18 days.

(21) Appl. No.: 15/560,081

(22) PCT Filed: Mar. 14, 2016

(86) PCT No.: PCT/US2016/022271
§ 371 (c)(1),
(2) Date: Sep. 20, 2017

(87) PCT Pub. No.: WO2016/153834
PCT Pub. Date: Sep. 29, 2016

(65) Prior Publication Data
US 2018/0080828 A1 Mar. 22, 2018

(30) Foreign Application Priority Data

Mar. 25, 2015 (EP) ...................... 15160693

(51) Int. Cl.
*G01J 3/50* (2006.01)
*H04N 5/225* (2006.01)
(Continued)

(52) U.S. Cl.
CPC ............... *G01J 3/508* (2013.01); *A61B 1/04* (2013.01); *A61B 1/06* (2013.01); *A61B 1/24* (2013.01);
(Continued)

(58) Field of Classification Search
CPC . G01J 3/508; G01J 3/52; G01J 3/0272; G02B 6/0096; G02B 27/144; G03B 9/08; A61B 1/04; A61B 1/06
(Continued)

(56) References Cited

U.S. PATENT DOCUMENTS 4,923,297 A * 5/1990 Arndt ....................... A61B 3/12
351/208
5,712,732 A * 1/1998 Street ................. G02B 27/0093
359/630
(Continued)

FOREIGN PATENT DOCUMENTS

JP 2003315150 11/2003
WO WO 2013-025688 2/2013
(Continued)

OTHER PUBLICATIONS

International Search report for PCT International Application No. PCT/US2016/022271 dated Aug. 24, 2016, 7 pages.

*Primary Examiner* — Hee-Yong Kim
(74) *Attorney, Agent, or Firm* — 3M Innovative Properties Company

(57) ABSTRACT

A dental imaging and illumination device. The device has an optical interface for emitting light from the device and for receiving light into the device. The device has a light source, a camera, a beam splitter and a color reference. The color reference and the light source are optically coupled via an optical path so that the light source can illuminate the color reference. This optical path bypasses the beam splitter. The device facilitates color measuring particularly in the field of dentistry.

19 Claims, 2 Drawing Sheets

(51) Int. Cl.
*F21V 8/00* (2006.01)
*G02B 27/14* (2006.01)
*G03B 9/08* (2006.01)
*G01J 3/52* (2006.01)
*G01J 3/02* (2006.01)
*A61B 1/04* (2006.01)
*A61B 1/06* (2006.01)
*A61B 1/24* (2006.01)
*A61B 5/103* (2006.01)
*A61C 13/08* (2006.01)
*A61B 5/00* (2006.01)

(52) U.S. Cl.
CPC .......... *A61B 5/0088* (2013.01); *A61B 5/1034* (2013.01); *A61C 13/082* (2013.01); *G01J 3/0272* (2013.01); *G01J 3/52* (2013.01); *G01J 3/524* (2013.01); *G02B 6/0096* (2013.01); *G02B 27/144* (2013.01); *G03B 9/08* (2013.01); *H04N 5/2256* (2013.01); *A61B 2560/0456* (2013.01); *H04N 2005/2255* (2013.01)

(58) Field of Classification Search
USPC .......................................................... 348/66
See application file for complete search history.

(56) References Cited

U.S. PATENT DOCUMENTS

| 6,384,917 | B1 | 5/2002 | Fradkin |
| 2006/0251408 | A1 | 11/2006 | Konno |
| 2009/0153858 | A1 | 6/2009 | Babayoff |
| 2014/0204239 | A1 | 7/2014 | Van den Hengel |

FOREIGN PATENT DOCUMENTS

| WO | WO 2014-043488 | 3/2014 |
| WO | WO 2015-148593 | 10/2015 |

\* cited by examiner

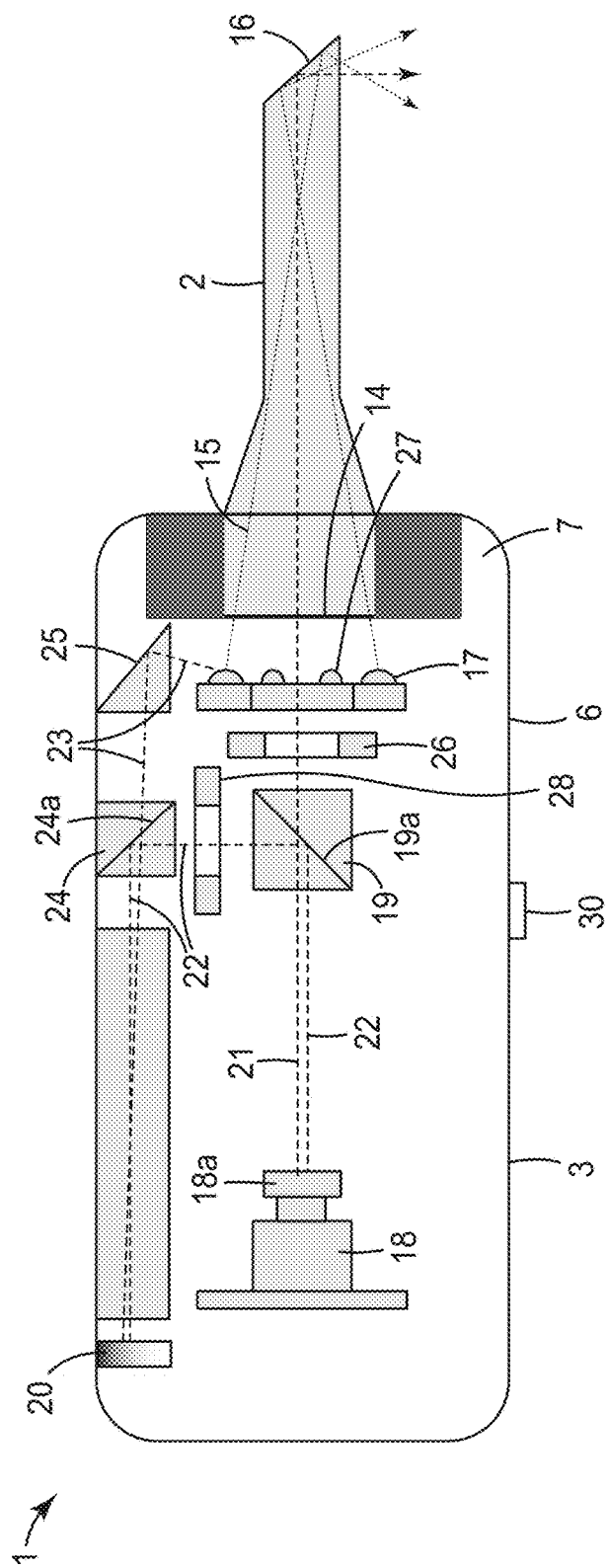
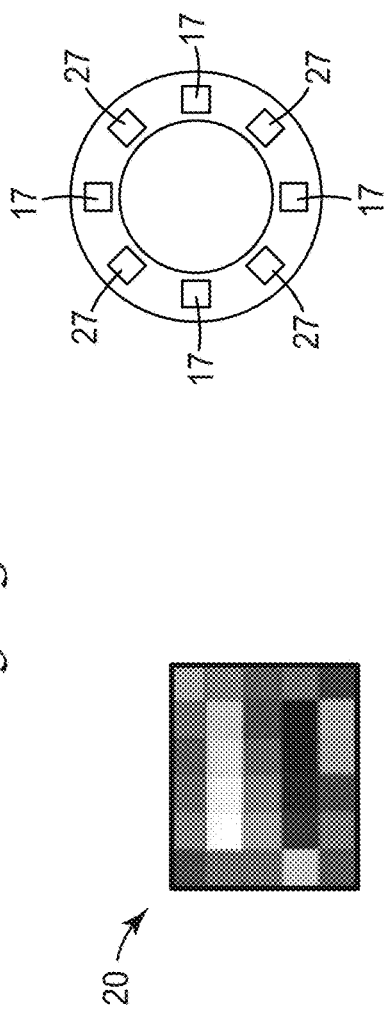

DENTAL IMAGING AND ILLUMINATION DEVICE

FIELD OF THE INVENTION

The invention relates to a dental imaging and illumination device. In particular the invention relates to a device which comprises a light source, a camera, a beam splitter and a color reference wherein the color reference can be illuminated by the light source under bypassing the beam splitter.

BACKGROUND ART

In dentistry it is a general desire to provide dental restorations which approximate the appearance of natural teeth. The appearance of natural teeth is on the one hand provided by color shades, and further by a certain translucency. A dental technician or a dental practitioner, for example, typically selects the color of the restorative material to be used for the dental restoration according to the teeth in a patient's mouth that are located next to the tooth or teeth to be restored. For example, the appearance of relevant teeth in a patient's mouth may be determined using shade guides. Exemplary shade guide types are available under the designations "VITA Classical Shade Guide" or "VITA Toothguide 3D-Master®" from the company VITA Zahnfabrik H. Rauter GmbH & Co. KG, Germany.

Further, there are electronic devices for measuring a color and/or a translucency of a tooth.
Such an electronic device is for example available under the designation SpectroShade™ from the company Medical High Technologies, Italy.

There are further electronic devices which integrate several functions, including illumination, light hardening, imaging and color measuring.

For example WO 2014/043488 A1 discloses a dental irradiation device which comprises a first light emitting unit for emitting blue light adapted for light hardening of a dental material. The device further comprises a second light emitting unit and an image sensing unit which are adapted for cooperation with each other for simultaneous illumination and image capturing. Image data captured by the device may be used by a computer for measuring a tooth color therefrom.

Although current devices may provide a variety of advantages there is still a desire to provide a device that is relatively convenient in handling. Further such a device is desirably inexpensive. There is also a desire to provide a device which can be used at a relatively high level of hygiene.

SUMMARY OF THE INVENTION

The invention relates to a dental imaging and illumination device. The device comprises: an optical interface for emitting light from the device and for receiving light into the device;
a first light source which is arranged within the device for emitting white light through the optical interface;
a camera;
a first beam splitter arranged in a first optical path between the camera and the optical interface, the first beam splitter being configured to pass light received via the optical interface toward the camera;
a color reference;
wherein the first beam splitter is further arranged in a second optical path between the camera and the color reference, the first beam splitter being configured to pass light from the color reference toward the camera; and
wherein the color reference and the first light source are optically coupled via a third optical path for the first light source to illuminate the color reference, which third optical path bypasses the first beam splitter.

The invention is advantageous in that it provides a multifunctional dental imaging and illumination device for intraoral use. Further, the device of invention is advantageous that it facilitates color measuring of a patient's tooth or teeth. In particular the invention provides for a maximized accuracy in color measuring at a maximized light efficiency in illumination as well as in imaging.

In one embodiment the color reference is a passive color reference. For example a standard color reference having a plurality of patches of a predetermined size, location and color may be used. Such a color reference is for example available under the designation Color Checker Pico from Edmund Optics, Germany. Such a standard color reference may for example exhibit twelve grayscale patches and sixteen color patches.

In one embodiment the device comprises a second light source which is arranged within the device for emitting blue light through the optical interface.

For the purpose of the present specification the term "blue light" refers to light having a wavelength within the range of about 430 nm to 500 nm, preferably within a range of about 430 nm to 480 nm. For the purpose of the present specification the term "white light" refers to light having a wavelength within a range of about 380 nm to 780 nm. Although white light may also comprise light at wavelengths overlapping with the range of wavelengths of blue light, white light preferably does not predominantly consist of light within the range of blue light but has significant portions of visible light at wavelengths outside the range of blue light. In contrast blue light preferably predominantly consists of light within a range of about 430 nm to 480 nm. Blue light may particularly not comprise light having a wavelength outside the range of about 430 nm to 480 nm at a substantial intensity or at all. In particular blue light may have a first portion of light within a range of about 430 nm to 480 nm and preferably does not have a significant second light portion within a range of 570 nm and 590 nm, wherein the maximum intensity of the second portion of light is preferably less than 10% and more preferably less than 1% of the maximum intensity of the first portion of light. Further blue light may not have a significant third light portion within the spectrum of visible light outside the range of 430 nm and 480 nm and outside the range of 570 nm to 590 nm, wherein the maximum intensity of any third portion of light is preferably less than 25% and more preferably less than 20% of the maximum intensity of the first portion of light.

In a preferred embodiment the device is configured for operation in a calibration mode, a polymerization mode and a color measuring mode. Further the device may be configured for operating in an imaging mode.

In the calibration mode the camera takes an image of the color reference and assigns the color information detected by the camera to color values stored in a memory of the device. The values stored in the memory are associated with respective patches of the color reference and therefore with respective (real) colors. Accordingly, a color information detected by the camera from a particular grayscale or color patch is assigned to the respective color value stored in the memory. Thus, the device may be configured to detect color information of light received by the camera via the first optical path, and to recognize a color associated with the color information based on the light received by the camera via the second optical path.

In the color measuring mode the camera is used to take at least one image through the optical interface, for example an image of an object outside the device. Based thereon the device analyses the color information detected at different locations of the image and recognizes those color information which are associated to stored color values to the color represented by the color value. Any color of intermediate color information can be calculated. In the imaging mode the camera is used to take at least one image through the optical interface, for example an image of an object outside the device. In contrast to the color measuring mode, in the imaging mode image information detected by the camera is preferably used to store and/or to display the detected image. Preferably the image(s) are displayed in real time as they are taken. Therefore the device may be used as intra-oral camera for diagnosis and/or patient education purposes. In the color measuring mode as well as in the imaging mode further the first light source is preferably activated during any image is taken by the camera.

In the polymerization mode the second light source is activated to emit blue light through the optical interface. The polymerization mode is preferably controlled such that the second light source is automatically deactivated after a predetermined period of time. The device is further preferably adapted to pre-select a particular predetermined time period from several time periods preset in the device.

In one embodiment the device is configured such that upon activation of the imaging mode the device automatically first switches in the calibration mode. After calibration (or after a predetermined time period provided for calibration), the device may automatically deactivate the calibration mode and activate the imaging mode. Thus prior to activation of the imaging mode the camera is automatically calibrated based on the color reference. The calibration mode may be activated manually at any time, in which case preferably the operation in the imaging mode is suspended. Further, the device may have functionality to automatically switch from the imaging mode to the calibration mode after a predetermined time period in which the imaging mode was activated has lapsed.

In an embodiment in the polymerization mode the second light source is activated for continuously emitting light. Further in the polymerization mode the imaging mode may be optionally activated simultaneously. Therefore a user may observe an object irradiated with blue light in the polymerization mode.

In one embodiment in the polymerization mode the first light source may be operated in a flash mode with the camera taking images synchronized on the flashes. Accordingly, the camera may only take an image while the first light source is activated. At the time an image is taken in the polymerization mode the blue light of the second light source is preferably activated also. Accordingly the captured image may have a blue undertone which however may be corrected electronically or by software. Therefore the device of the invention may be adapted to provide true color images of an object which is irradiated with blue light in the polymerization mode. This function provides a relatively convenient use of the device.

In one embodiment the device has an activator button, a selector button and a mode switch. The device may be configured such that an actuation (for example pushing) of the activator button causes the device to activate (switch on). Preferably the device automatically activates in the calibration mode and may automatically switch into the color measuring mode after. The device may be configured such that each actuation (for example pushing) of the mode switch causes the device to consecutively switch from the color measuring mode, to the imaging mode, to an optional combined imaging and polymerization mode, to the polymerization mode, back to the calibration mode and so on. The skilled person will be able to provide the same device with the different modes switchable in any other order.

In an embodiment the first beam splitter comprises a first reflector in the form of first semi-transparent mirror. The camera, the first semi-transparent mirror and the optical interface are preferably arranged in an optical relationship with each other such that the first beam splitter passes light on the first optical path by transmission through the first semi-transparent mirror. A semi-transparent mirror as referred to herein may be formed by a partially reflective surface, for example a glossy metal or metal coat, or a dielectric coating providing reflectivity by optical interference. Further the semi-transparent mirror be formed by a dichroic mirror. The first semi-transparent mirror may have a reflection to transmission ratio of 50% to 50%. Other ratios may be selected as appropriate.

In a further embodiment the device comprises a second reflector arranged in the second optical path so as to reflect light from the color reference toward the first beam splitter. In particular, the device may comprise a second beam splitter which comprises the second reflector. The second beam splitter is preferably arranged in both, the second and the third optical path, so as to pass light from the first light source toward the color reference and to pass light from the color reference toward the first beam splitter. The second reflector may be formed by a second semi-transparent mirror. The first light source, the second semi-transparent mirror and the color reference are preferably arranged in an optical relationship with each other such that the second beam splitter passes light on the third optical path by transmission through the second semi-transparent mirror. The second semi-transparent mirror has preferably a reflection to transmission ratio of 50% to 50%. Again, other ratios may be selected as appropriate.

In a further embodiment the second reflector may comprise a reflective surface positioned such that light from the color reference is directed towards the first beam splitter while allowing light from the first light source to reach the color reference.

In a further embodiment the device comprises a third reflector in the third optical path. The third reflector is formed by a mirror or prism. The third reflector is preferably arranged such that a portion of a light cone emitted from the first light source impinges on the third reflector. Further, with reference to an axis of symmetry of such a light cone the third reflector is preferably arranged such that light is reflected from the third reflector approximately parallel or parallel to the axis of symmetry, but in an opposite direction than the direction in which the first light source emits light.

In a further embodiment the device comprises a first shutter arranged in the first optical path. A shutter as referred to herein may comprise a mechanical shutter, for example one having movable light impermeable blades, or a switchable optical element, like for example one which is based on a liquid crystal layer which crystals can be oriented by an electrical field. The first shutter is operable between an open position in which the first shutter permits light to pass through and a closed position in which the first shutter blocks light. The device further preferably comprises a second shutter arranged in the second optical path. The second shutter is preferably operable between an open position in which the second shutter permits light to pass through and a closed position in which the second shutter blocks light. Accordingly in the calibration mode the first shutter may be closed to prevent light from the optical interface to impinge into the camera, and the second shutter may be open for allowing light from the color reference to impinge into the camera. In the color measuring (or imaging) mode the second shutter may be closed to prevent light from the color reference to impinge into the camera, and the first shutter may be open to allow light from the optical interface to impinge into the camera.

In a further embodiment the device is controlled to perform the following steps upon activation of the device:
(i) activating the first light source, closing the first shutter and opening the second shutter in any order or simultaneously;
(ii) detecting color information from light received by the camera;
(iii) using the detected color information as color reference; and
(iv) opening the first shutter and closing the second shutter in any order or simultaneously.

The device may be configured to perform steps (i), (ii), (iii), and (iv) consecutively and automatically.

In an embodiment the first light source extends circumferentially and forms an opening through which the first optical path extends. The first light source may comprise a plurality of LEDs (preferably white LEDs) which are configured to emit light at a cone of radiation or light cone. At least a part of the LEDs are oriented such the cone of radiation overlaps with the optical interface. The second light source may also extend circumferentially and may form an opening through which the first optical path extends. The second light source may comprise a plurality of LEDs (preferably blue LEDs) which are configured to emit light at a cone of radiation or light cone. At least a part of the LEDs are oriented such the cone of radiation overlaps with the optical interface. The first and second light source may be combined on a common ring-shaped circuit board, with the white and blue LEDs arranged in an alternating fashion. The plurality of blue and white LED's may be uniformly distributed on the ring-shaped circuit board.

In a further embodiment the device comprises a user interface for indicating color information. The user interface may be integrated in the device, for example in the form of a display. Such a display may indicate the color information in the form of a code of the VITA tooth color scheme. Alternatively or additionally the user interface may comprise an external device (for example a computer) for displaying a tooth color code or another color code (for example RGB or L*a*b*). The device may comprise a data interface (for example Bluetooth®) for communication with the external device.

In one embodiment the device comprises a body and a light guide. The light guide has a proximal end and an opposite distal end and is preferably configured for guiding light between the proximal end and the distal end. The body may comprise a receptacle for removably receiving the proximal end of the light guide. Further, the receptacle may comprise the optical interface. The optical interface is preferably optically coupled with the proximal end of the light guide. Thus, an object arranged in the vicinity of the distal end may be imaged and/or illuminated by the device.

In a further embodiment the first optical path and the light guide are, in combination, configured for transmission of an image. The light guide may for example be formed of a solid transparent wand extending in between the distal end and the proximal end. Such a wand may be made of glass or a high transparent polymer like PMMA (polymethyl methacrylate), or formed by a hollow tube having inwardly a reflective surface. The device of this embodiment does not require any additional optical elements, for example lenses, for guiding an image from the distal end of the light guide toward the optical interface.

In a further embodiment the device is battery powered. Therefore the device may comprise a rechargeable battery. Accordingly the device may be a cordless device.

In one embodiment the camera has a focusing unit. The focusing unit preferably has a working distance of 150 mm±50 mm.

In a further embodiment the first and second optical paths have substantially the same length. The length of the first optical path and the length of the second optical path may be in a ratio of 70% relative to each other. In case the device has a light guide, the length of the first optical path together with the length of the light guide may form an overall first optical path which substantially corresponds in length with the length of the second optical path. The length of the overall first optical path and the length of the second optical path may be in a ratio of 125% relative to each other.

BRIEF DESCRIPTION OF THE FIGURES

FIG. 2 is a schematic cross-sectional view of a dental imaging and illumination device according to an embodiment of the invention;

FIG. 3 is a detail view of a color reference as it may be used with a dental imaging and illumination device according to an embodiment of the invention; and FIG. 4 is a detail view of a first and second light source as they may be used with a dental imaging and illumination device according to an embodiment of the invention.

DETAILED DESCRIPTION OF THE INVENTION

Figure 1:
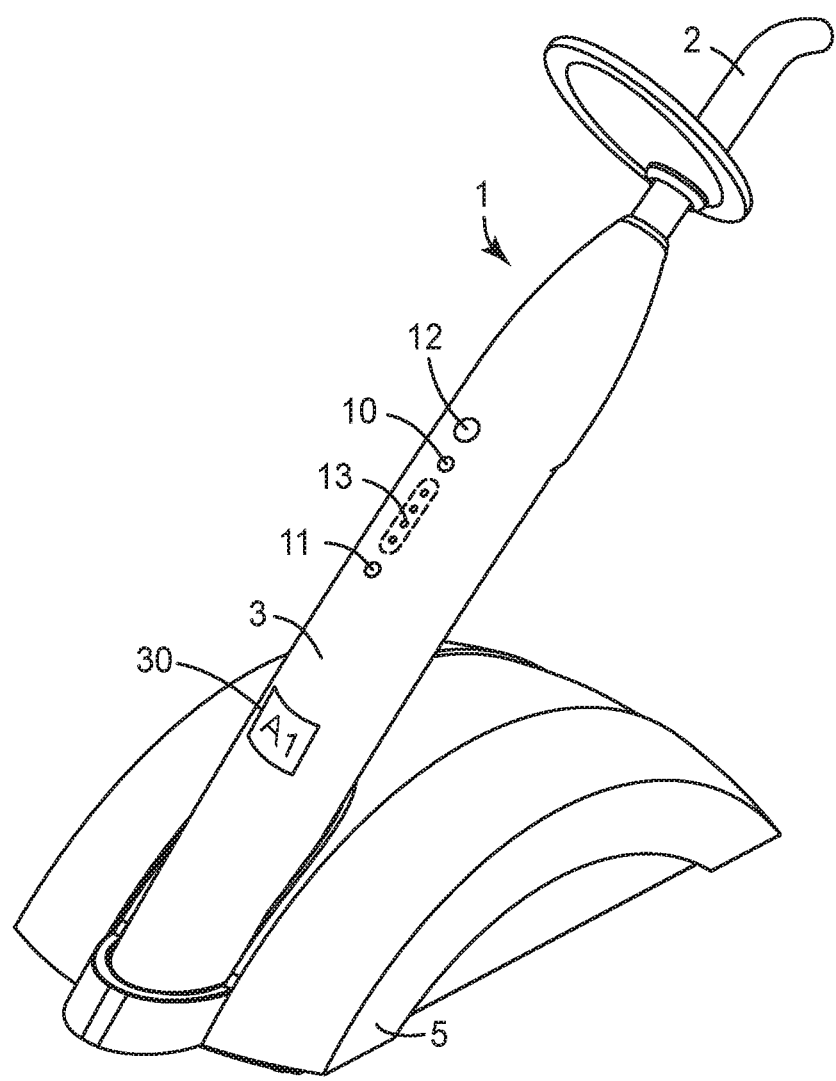
FIG. 1 is a perspective view of a dental imaging and illumination device according to an embodiment of the invention.

FIG. 1 shows an exemplary dental imaging and illumination device 1. The device 1 has a body 3 which houses all electronic components. The device 1 further has a light guide 2 which makes the device 1 suitable for intra-oral use. The light guide 2 is detachable from the body 3, and because the light guide 2 is free of any electronic components it can be disinfected easily, for example at high temperatures and using aggressive disinfectants. The device 1 is configured for taking an image or a series of images. Therefore the device 1 has an internal camera (not visible in this view) for receiving the image. The device 1 further has a first and a second light source (illustrated in FIG. 4 and indicated as 17, 27, respectively) for emitting light from the device 1. The first light source is configured to emit white light and serves for illumination of an object to be imaged by the camera. The second light source is configured to emit blue light and serves for polymerizing a hardenable dental material. Accordingly the device 1 is generally configured for imaging by means of the camera and the first light source and for polymerizing a dental material by means of the second light source.

The device 1 is battery powered and can be removably placed in a base 5 for recharging the battery. The base 5 has a power supply for charging the device 1 when the device is placed in the base 5. Such a power supply may comprise physical electric contacts for contacting corresponding contacts of the device 1, or an induction coupling for coupling with a corresponding induction coupling in the device 1.

The exemplary device 1 has an activator button 10, a selector button 11 and a mode switch 12. The device is configured such that pushing the activator button 10 causes the device to activate (or to switch on). Optionally, the device is configured such that a push on the activator button 10 during the device is activated causes the device to deactivate (or to switch off) and a push on the activator button 10 during the device is deactivated causes the device to activate. The mode switch 12 enables the device 1 to be switched between a calibration mode, a polymerization mode, an imaging mode and a color measuring mode. Each push on the mode switch causes the device to activate one of the three modes, for example in a consecutive order. In the calibration mode the camera is adjusted in color as described in further detail below. For displaying one or more colors the device may have a display 30, which in the example displays a tooth color code of the so-called VITA color scheme determined from the measured color(s). In the polymerization mode the device 1 emits blue light and in the imaging mode the camera is used to capture an image during white light is emitted from the device 1. The selector button 11 enables a pre-selection of a time period for which the device automatically operates in the polymerization mode and after which the polymerization mode automatically deactivates. In the device 1 the selector button 11 typically allows the user to pre-select between different default time periods. For example, each push on the selector button 11 may increase the operating time period by a certain time unit. Upon reaching an available maximum a further push on the selector button 11 resets the time period to a minimum again. Thus, a user can pre-select a certain time period (indicated on the device by LEDs 13) by pushing the button as often as required. The time period is typically selected in accordance to the material used, the thickness of the material to be hardened and the desired degree of polymerization.

The skilled person will recognize alternative buttons or equivalents for replacing a button. Instead of a push button, for example a touch sensor, a tumbler switch, a rotary switch or any other appropriate switch may be used.

FIG. 2 shows the same device 1 in some further detail. The body 3 may in particular comprise a housing 6 having an opening that is sealed by an optical interface 14. The housing 6 is made of a light blocking material and is preferably made of metal or plastic. The plastic may itself be opaque and optionally has at least one additional light blocking coating, for example an aluminum coating. The optical interface 14 is formed by a transparent cover, for example a glass cover.

The optical interface 14 serves for emitting light from the device 1 and for receiving light into the device 1. In the example shown the optical interface 14 is formed in a mouth-piece 7 of the device 1. The mouth-piece 7 is configured for attachment with the light guide 2. The light guide 2 has a proximal end 15 and a distal end 16. The mouth-piece 7 is configured such that the proximal end 15 of the light guide 2 and the optical interface 14 are optically coupled, when the light guide 2 is attached to the mouth piece 7. In the example, the mouth-piece has a receptacle to receive the proximal end 15 of the light guide 2 therein. The skilled person will however recognize that likewise a light guide may be furnished with a mount which forms a receptacle for receiving a pin-shaped mouth-piece therein. The light guide 2 of the example is made of a hollow tube having an inward mirrored surface. The tube thus directs light from an external object at the distal end 16 towards the proximal end 15. Accordingly the light guide 2 is configured for guiding light between the proximal end 15 and the distal end 16. Although the light guide 2 is the Figure is illustrated as a straight structure the light may alternatively be curved, as for example shown in FIG. 1.

The device 1 has a first light source 17 which is arranged within the device for emitting white light. The first light source 17 has a dual function in that the first light source 17, firstly, is arranged to emit white light toward the optical interface 14 and, secondly, (preferably at the same time) to illuminate a color reference 20 that is arranged within the body 3. The color reference 20 is used for calibrating camera 18 as described in further detail below.

In the example the first light source 17 has four white LEDs (see FIG. 4) which each are oriented with their light emitting side toward the optical interface 14. The second light source 27 has four blue LEDs (see FIG. 4) which each are also oriented with their light emitting side toward the optical interface 14. As illustrated in FIG. 4 the blue and white LEDs are arranged in an alternating fashion uniformly distributed over the circumference of a circle. The skilled person will be able to select other numbers of LEDs depending on the light intensity required and the light intensity provided by one LED. Preferably the LEDs are arranged in a circular arrangement and uniformly distributed over the circumference of the circle.

The camera 18 is arranged such that it can capture an image received through the optical interface 14. The camera 18 has a light sensing side with a focusing unit 18a for producing a real image from light received through the optical interface 14. The camera 18 may be based on CCD or CMOS sensing electronics. Accordingly, the real image may be sensed by photo sensors of the CCD or CMOS element of the camera 18. In more particular the camera 18 is oriented with its light sensing side in generally the same dimension as the light emitting side of the first light source 17. However the camera 18 is arranged in a direction opposite of the direction in which first light source 17 emits light. In other words the camera 18 is arranged optically behind the first light source 18. Thus, light emitted from the first light source is not directly emitted toward the camera 18.

A first optical path 21 is established between the camera 18 and the optical interface 14. As illustrated the first optical path 21 extends straight between the camera 18 and the optical inter face 14 and extends through a plane in which the first light source 17 is arranged. This is enabled because the light source 17 is formed by a ring-shaped circuit board which carries the LEDs, so that the camera 18—in a manner of speaking—"looks through" the hole of the ring-shape light source 17.

A first beam splitter 19 is arranged in the first optical path 21 between the camera 18 and the optical interface 14. The first beam splitter is configured to pass light received via the optical interface 14 toward the camera 18. In the example first beam splitter 19 comprises a first semi-transparent mirror 19a. The first beam splitter 19 is arranged with the first semi-transparent mirror 19a such that light on the first optical path 21 from the optical interface 14 toward the camera 18 travels straight through the beam splitter 19. In other words the camera 18, the first semi-transparent mirror 19a and the optical interface 14 are arranged in an optical relationship with each other such that the first beam splitter 19 passes light on the first optical path by transmission through the first semi-transparent mirror 19a.

A second optical path 22 is established between the color reference 20 and the camera 18 via the first beam splitter 19. The passive color reference 20 is shown in greater detail in FIG. 3. The color reference in the example has thirty square shaped color samples in a matrix of five rows and six columns, each sample having a unique predetermined color. A controller of the device 1 stores the nominal colors and locations of the colors associated with the color reference 20. Therefore, an image of the color reference taken by the camera 18 can be used to adjust the output of the camera in accordance with the nominal colors stored. With the information stored in the controller that for example the color sample in the first column and the third row of the color reference is a particular yellow any identical output of the camera corresponding to the output provided during calibration can be recognized as yellow. The same principle can be applied for determining other colors. Intermediate colors which are not present on the color sample can be calculated by the controller based on the photo sensors and filters used within the camera. Thus, the device 1 can be used as a color measuring device.

The second optical path 22 is optically coupled into the first optical path 21 by the beam splitter 19. In particular the second optical path 22 is laterally coupled into the first optical path 21. Hence, the first and second optical paths 21, 22 partly coincide and partly do not coincide. The coinciding part of the first and second optical paths 21, 22 are provided between the camera 18 and the first beam splitter 19. This is provided by orientation of the first semi-transparent mirror 19a in an angle of, in the example, about 45 degrees. The skilled person will be able to optically couple the second optical path 22 into the first optical path 21 at other angles according to the general principles of optics.

The first beam splitter 19 is arranged with the first semi-transparent mirror 19a such that light on the second optical path 22 from the color reference 20 toward the camera 18 is deviated by the first semi-transparent mirror 19a. Accordingly the beam splitter 19 has a first reflector in the form of the first semi-transparent mirror 19a. In other words, the color reference 20, the first semi-transparent mirror 19a and the camera 18 are arranged in an optical relationship with each other such that the first beam splitter 19 passes light on the second optical 22 path by reflection through the first semi-transparent mirror 19a.

Further, a third optical path 23 is established between the first light source 17 and the color reference 20. The color reference 20 and the first light source 17 are optically coupled via the third optical path 23 such that the first light source 17 can illuminate the color reference 20. The third optical path 23 bypasses the first beam splitter 19. Therefore interferences between light of an image received from the optical interface 14 and light emitted from the first light source 17 can be minimized.

The device 1 has a second beam splitter 24 which comprises a second reflector 24a in the form of a second semi-transparent mirror 24a. The second beam splitter 24 is arranged in both, the second and the third optical path 22, 23, so as to pass light from the first light source 17 toward the color reference 20 and to pass light from the color reference 20 toward the first beam splitter 19. In particular the first light source 17, the second semi-transparent mirror 24a and the color reference 20 are arranged in an optical relationship with each other such that the second beam splitter 24 passes light on the third optical path 23 by transmission through the second semi-transparent mirror 24a. Further, the color reference 20, the second semi-transparent mirror 24a and the camera 18 are arranged in an optical relationship with each other such that the second beam splitter 24 passes light on the second optical 22 path by reflection by the second semi-transparent mirror 24a. As illustrated the third optical path 23 is coupled into the second optical path 21. Hence, the second and third optical paths 22, 23 partly coincide and partly do not coincide. The coinciding part of the second and third optical paths 22, 23 are provided between the color reference 20 and the second beam splitter 24. The third optical path 23 is optically coupled into the second optical path 22 at the second semi-transparent mirror 24a, where the second optical path 22 is deviated by the second beam splitter 24. This is provided by orientation of the second semi-transparent mirror 24a in an angle of, in the example, about 45 degrees. Overall the second optical path 22 extends along a U-shape and thus is deviated by 180 degrees by the first and second beam splitter 19, 24 in combination. It is preferred that the length L2 of the second optical path 22 approximates the length L1 of the first optical path 21 plus a distance D between the proximal end 15 and the distal end 16 of the light guide. In devices in which no light guide is used, the length L2 of the second optical path 22 should approximate the length L1 of the first optical path 21. Preferably, the ratio L2:(L1+D) or L2:L1 is at least 80%. The skilled person will recognize that although the presence of the second beam splitter 24 provides certain advantages, for example with respect to a compact design enabled by guiding the second optical path 22 in a U-shaped fashion, in another embodiment the color reference may be arranged so that it directly faces the first beam splitter 19. In this case the second beam splitter 24 is optional.

In the example a portion of the light emitted by the light source 17 is reflected by a third reflector in the form of a prism 25 or mirror (not shown). The skilled person will recognize that in the example in which the color reference 20 directly faces the second beam splitter 24 also the prism 25 is optional. This is because a portion of the light (for example scattered light) emitted from the first light source 17 can illuminate the color reference 20 if oriented toward the first beam splitter 19. The prism 25 is at least partially arranged within the light cone of at least one of the LEDs of the light source 17. Preferably the prism 25 is arranged outside the center axis of the light cone of the same LED. Accordingly, the prism 25 does not block a substantial amount of light emitted from the LED, but receives a sufficient amount of light for illuminating the color reference 20. In the example the color reference is arranged optically behind the light source 17 and also behind the camera 18. This helps further minimizing any interference between light used for illuminating the color reference and the light of any image captured by the camera 18.

The device 1 further has a first shutter 26 which is arranged in the first optical path 21 and a second shutter 28 in the second optical path 22. In particular the first shutter 26 is arranged between the first beam splitter 19 and the optical interface 14 and the second shutter is arranged between the first beam splitter 19 and the second beam splitter 24. The first and second shutter 26, 28 each may be formed by a motor driven iris, for example as used in digital cameras. The first and second shutter 26, 28 further are configured for largely or entirely block light on the respective first and/or second optical path 26, 28. In the calibration mode the first shutter 26 may be closed and the second shutter 28 may be open so that the camera 18 receives light substantially only via the second optical path 22. Further, in the imaging mode and in the color measuring mode the first shutter 26 may be open and the second shutter 28 may be closed so that the camera 18 receives light substantially only via the first optical path 22. Thus, calibration and imaging can be performed independently and substantially without interference from each other. The skilled person will recognize that the presence of the first and second shutter 26, 28 contribute to a maximized accuracy, for example in the color measuring. However, the skilled person will further recognize that in another example shutters may be optional and therefore may be omitted, for example for the sake of reducing costs at lower but still acceptable measuring accuracy. The first and second shutter 26, 28 may further be closed during activation of the polymerization mode. Thus, the camera 18 may be protected from intense light used for polymerization. However, the device 1 is preferably configured such that the first shutter 26 can be opened in the polymerization mode. Therefore the device 1 is adapted for performing the polymerization mode and the imaging mode simultaneously. This allows monitoring of the material during polymerization, and further enables a user of the device 1 to control the position of the device 1 relative to the material during polymerization.

In the color measuring mode the second light source 27 is deactivated and only the first light source 17 and the camera 18 are activated. Due to the calibration by means of the color reference 20 the device 1 is configured to measure the colors of the image captured by the camera. The measured colors or an overall color averaged from the measured colors may be displayed on the display 30 of the device. While a display of an averaged color directly on the device 1 is advantageous, the device 1 preferably has an interface to transmit the measured colors, for example in the form of data representing a color landscape on an image captured by the camera, to an external unit, for example a computer. The color information may for example be used in a computer with a dental CAD system for designing the dental restoration based on a corresponding color gradation. Such an interface is preferably a wireless data interface, like Bluetooth®.

What is claimed is:

1. A dental imaging and illumination device, comprising:
   an optical interface for emitting light from the device and for receiving light into the device;
   a first light source which is arranged within the device for emitting white light through the optical interface;
   a camera;
   a first beam splitter arranged in a first optical path between the camera and the optical interface, the first beam splitter being configured to pass light received via the optical interface toward the camera;
   a color reference;
   wherein the first beam splitter is further arranged in a second optical path between the camera and the color reference, the first beam splitter being configured to pass light from the color reference toward the camera; and
   wherein the color reference and the first light source are optically coupled via a third optical path for the first light source to illuminate the color reference, which third optical path bypasses the first beam splitter.

2. The device of claim 1, being configured to detect color information of light received by the camera via the first optical path, and to recognize a color associated with the color information based on the light received by the camera via the second optical path.

3. The device of claim 1, wherein the first beam splitter comprises a first reflector in the form of first semi-transparent mirror, wherein the camera, the first semi-transparent mirror and the optical interface are arranged in an optical relationship with each other such that the first beam splitter passes light on the first optical path by transmission through the first semi-transparent mirror.

4. The device of claim 3, wherein the first semi-transparent mirror has a reflection to transmission ratio of 50% to 50%.

5. The device of claim 1, comprising a second reflector arranged in the second optical path so as to reflect light from the color reference toward the first beam splitter.

6. The device of claim 5, comprising a second beam splitter which comprises the second reflector, the second beam splitter being arranged in both, the second and the third optical path, so as to pass light from the first light source toward the color reference and to pass light from the color reference toward the first beam splitter.

7. The device of claim 6, wherein the second reflector is formed by a second semi-transparent mirror, wherein the first light source, the second semi-transparent mirror and the color reference are arranged in an optical relationship with each other such that the second beam splitter passes light on the third optical path by transmission through the second semi-transparent mirror.

8. The device of claim 7, wherein the second semi-transparent mirror has a reflection to transmission ratio of 50% to 50%.

9. The device of claim 1, comprising a third reflector in the third optical path.

10. The device of claim 9, wherein the third reflector is formed by a mirror or prism.

11. The device of claim 1, further comprising a first shutter arranged in the first optical path, the first shutter being operable between an open position in which the first shutter permits light to pass through and a closed position in which the first shutter blocks light.

12. The device of claim 1, further comprising a second shutter arranged in the second optical path, the second shutter being operable between an open position in which the second shutter permits light to pass through and a closed position in which the second shutter blocks light.

13. The device of claim 11, being controlled to perform the following steps upon activation of the device:
   activating the first light source, closing the first shutter and opening the second shutter in any order or simultaneously;
   detecting color information from light received by the camera;
   using the detected color information as color reference; and
   opening the first shutter and closing the second shutter in any order or simultaneously.

14. The device of claim 1, wherein the first light source extends circumferentially and forms an opening through which the first optical path extends.

15. The device of claim 14, wherein the first light source comprises a plurality of LEDs which are configured to emit light at a cone of radiation, wherein at least a part of the LEDs are oriented such the cone of radiation overlaps with the optical interface.

16. The device of claim 1, further comprising a user interface for indicating color information.

17. The device of claim 1, comprising a body and a light guide, the light guide having a proximal end and an opposite distal end and being configured for guiding light between the proximal end and the distal end, the body comprising a receptacle for removably receiving the proximal end of the light guide, which receptacle comprises the optical interface, and wherein the optical interface is optically coupled with the proximal end of the light guide.

18. The light device of claim 17, wherein the first optical path and the light guide are, in combination, configured for transmission of an image.

19. The light device of claim 1, comprising a second light source which is arranged within the device for emitting blue light through the optical interface.

* * * * *

UNITED STATES PATENT AND TRADEMARK OFFICE
CERTIFICATE OF CORRECTION

PATENT NO. : 10,458,848 B2  
APPLICATION NO. : 15/560081  
DATED : October 29, 2019  
INVENTOR(S) : Johannes Fink Page 1 of 1

It is certified that error appears in the above-identified patent and that said Letters Patent is hereby corrected as shown below:

In the Specification

Column 2  
Line 5, delete "from the color reference toward the camera; and" and insert the same on Column 2, Line 4, as a continuation of the same paragraph.

Column 2  
Line 10, delete "optical path bypasses the first beam splitter." and insert the same on Column 2, Line 9, as a continuation of the same paragraph.

Column 5  
Line 34, after "such" insert -- that --.

Column 5  
Line 41, after "such" insert -- that --.

In the Claims

Column 12  
Line 61, in Claim 15, after "such" insert -- that --.

Signed and Sealed this  
Eighteenth Day of August, 2020

Andrei Iancu  
*Director of the United States Patent and Trademark Office*